United States Patent [19]

Kessen et al.

[11] Patent Number: 4,684,750

[45] Date of Patent: Aug. 4, 1987

[54] PROCESS FOR THE PRODUCTION OF 2-ETHYL-HEXANOL

[75] Inventors: Gunther Kessen, Oberhausen; Boy Cornils, Hofheim; Wilhelm Gick, Duisburg; Ernst Wiebus; Joseph Hibbel, both of Oberhausen; Hanswilhelm Bach, Duisburg; Wolfgang Zgorzelski, Oberhausen-Buschhausen, all of Fed. Rep. of Germany

[73] Assignee: Ruhrchemie Aktiengesellschaft, Fed. Rep. of Germany

[21] Appl. No.: 900,389

[22] Filed: Aug. 26, 1986

[30] Foreign Application Priority Data

Aug. 29, 1985 [DE] Fed. Rep. of Germany ....... 3530839

[51] Int. Cl.$^4$ ................... C07C 29/16; C07C 31/125
[52] U.S. Cl. ................... 568/883; 568/882
[58] Field of Search ................... 568/883, 882, 881

[56] References Cited

U.S. PATENT DOCUMENTS

| 3,118,954 | 1/1964 | Robbins et al. | 568/883 |
|---|---|---|---|
| 3,127,451 | 3/1964 | Berkeley et al. | 568/882 |
| 3,248,428 | 4/1966 | Porter et al. | 568/882 |
| 3,272,873 | 9/1966 | Porter et al. | 568/881 |
| 3,288,866 | 11/1966 | Cooper | 568/881 |
| 3,491,158 | 1/1970 | Reich | 568/881 |
| 3,763,247 | 10/1973 | Lemke et al. | 568/882 |
| 4,138,588 | 2/1979 | Tummes et al. | 568/881 |
| 4,374,278 | 2/1983 | Bryant et al. | 568/882 |
| 4,426,541 | 1/1984 | King | 568/883 |
| 4,426,542 | 1/1984 | Barker et al. | 568/883 |

FOREIGN PATENT DOCUMENTS

| 0052999 | 1/1982 | European Pat. Off. | 568/882 |
|---|---|---|---|
| 406823 | 4/1974 | U.S.S.R. | 568/882 |
| 478830 | 10/1975 | U.S.S.R. | 568/882 |
| 692824 | 10/1979 | U.S.S.R. | 568/881 |

*Primary Examiner*—J. E. Evans
*Attorney, Agent, or Firm*—Jordan B. Bierman

[57] ABSTRACT

A process for the production of 2-ethyl-hexanol comprising reacting propene with carbon monoxide and hydrogen, in the presence of an aqueous catalyst containing rhodium and at least one sulfonated triarylphosphine, to form an aqueous phase and an organic phase, said organic phase comprising a mixture of materials having boiling points lower than that of n-butanal and substances having boiling points equal to or higher than that of n-butanal, said materials including i-butanal, separating said material from said substances, subjecting said substances to aldol condensation, in the presence of aqueous alkali, to form 2-ethyl hexenal, first hydrogenating said 2-ethyl-hexenal in a gas phase in the presence of a first hydrogenation catalyst and thereafter hydrogenating said 2-ethyl-hexenal in a liquid phase to form 2-ethyl-hexanol in the presence of a second hydrogenation catalyst.

10 Claims, No Drawings

PROCESS FOR THE PRODUCTION OF 2-ETHYL-HEXANOL

The present invention is directed to a process for the production of 2-ethyl-hexanol; more particularly, to a process which results in improved efficiency, both in conversion and selectivity.

This compound is usually prepared by the hydroformylation of propene yielding a reaction mixture which contains n-butanal, as well as i-butanal and other reaction products. The pure n-butanal is separated from the reaction mixture by distillation and is subsequently subjected to aldolisation to form the corresponding butyraldol. This product is heated, water splits off, and 2-ethyl-hexenal is formed. This compound is then hydrogenated in the presence of appropriate catalysts to form the desired 2-ethyl-hexanol which is then purified in a multi-step distillation process.

A primary use of this product is in the production of dioctylphthalate, which is a preferred and commonly used plasticizer for polyvinylchloride. Such plasticizers are required to be extremely pure and colorless in order to function properly in the polymerization process. Therefore, the starting material, which is the object of the present invention, must also meet these strict standards. Thus, prior belief that the n-butanal which is used as the starting material for the adolisation must be in extremely pure form.

When the olefin (propene) is hydroformylated, i-butanal is an undesired impurity which is formed along with the n-butanal. It has been recognized by the prior art that the composition of the mixture resulting from hydroformylation can be altered by a judicious selection of reaction conditions. Thus, pressure, temperature, residence period, as well as the nature and composition of the catalyst, all will have an effect on the reaction products. However, even by adjusting parameters of this kind, it is not possible to prevent the formation of unwanted i-butanal.

The presence of this impurity in the mixture interferes with the production of the desired end product (2-ethyl-hexanol) because it impairs the quality thereof, even if it is only present in small amounts. As a result, it has been believed that it is necessary to remove the i-butanal (as well as the other by-products) from the hydroformylation reaction mixture so that substantially pure n-butanal is used as the starting material for the aldolisation.

A typical process of this type is described in American Chemical Society Symp. Ser. 1981 (Monohydric Alcohols), 159, Pages 71-85. In this process, the hydroformylation of propene takes place at low pressure in the presence of a rhodium catalyst which contains excess triphenylphosphine to form a reaction mixture.

This mixture is separated into three fractions using two distillation columns. In the first column, the i-butanal and lower boiling materials are distilled off. The residue is then conveyed to the second column wherein the pure n-butanal comes off the top, while the higher boiling materials are drawn off the bottom. The n-butanal is then subjected to the aldol condensation in the presence of aqueous sodium hydroxide at temperatures of 110° to 120° C., with a residence period of approximately 60 seconds. During the reaction, water is split off and 2-ethyl-hexenal is formed, along with small amounts of n-butanal, trimeric n-butanal, and 2-ethyl-hexenal.

Since the ethyl-hexenal is insoluble in water, it is easily separated from the aqueous alkali. The latter is recycled into the aldol condensation. The raw 2-ethyl-hexenal is then hydrogenated to the desired 2-ethyl-hexanol and subsequently purified by distillation.

Such process as are known in the prior art allow for only slight improvements in the yields of commercially valuable products. Nonetheless, in view of the large demand for pure 2-ethyl-hexanol, many attempts have been made to increase the yield. The product is of such commercial importance that even a small increase in yield will result in substantial savings.

It should be noted that there are serious disadvantages to the prior art two-step distillation used to recover pure n-butanal from the crude hydroformylation product. In the first place, extremely complicated distillation apparatus is required. Furthermore, n-butanal is quite reactive and, when heated, tends to condense to form unwanted higher boiling materials. The more the hydroformylation product is subjected to thermal loading during destillative work-up, the higher the n-butanal losses are.

It is, therefore, among the objects of the present invention to provide a process for the production of 2-ethyl-hexanol which will simplify the separation of n-butanol from its reaction mixture. It is also among the objects of the present invention to provide the foregoing simplification and to increase the yield of the desired 2-ethyl-hexanol. At the same time, it is a further object of the present invention to insure the required purity and color of the end product.

To that end, the present invention is a process for the production of 2-ethyl-hexanol comprising reacting propene with carbon monoxide and hydrogen in the presence of an aqueous catalyst containing rhodium and at least one sulfonated triaryl phosphine. In this reaction an organic phase is formed in addition to the aqueous phase already present.

The organic phase comprises a mixture of materials having boiling points lower than that of n-butanal and substances having boiling points equal to or higher than that of n-butanal. The i-butanal impurity is found in the materials, while the desired n-butanal is in the substances.

The materials are separated from the substances, as by distillation, and the substances are then subjected to aldol condensation in the presence of aqueous alkali, thus forming 2-ethylhexenal. It is unnecessary, in the present process, to insolate pure n-butanal from the reaction mixture.

The 2-ethylhexenal is first hydrogenated in the gas phase in the presence of a first—preferably fixed bed—hydrogenation catalyst and, thereafter, further hydrogenated in the liquid phase in the presence of a second hydrogenation catalyst to form the desired 2-ethyl-hexanol. The final product is then purified by distillation in the usual manner.

The preparation of n-butanal in accordance with the hydroformylation step of the foregoing process is described in, for example, DE 26 27 354 C3. Temperatures of between 50° and 120° C. are used. DE 32 34 701 A1 teaches the use of a temperature range of 90° to 150° C. for the conversion of olefins of this type.

It has been found that the hydroformylation of propene takes place advantageously at temperatures of 50° to 140° C., in particular, from 70° to 130° C., and most preferably from 90° to 125°. Pressures may range from 0.1 to 30 MPa, particularly from 0.5 to 10 MPa, and most preferably from 1 to 6 MPa. The mole ratio of rhodium to sulfonated triaryl phosphines is from 1:3 to 1:300, particularly from 1:5 to 1:250, and most desirably from 1:10 to 1:200. The volume ratio of the organic phase to the aqueous phase is 1:1 to 1:100, particularly 1:4 to 1:40, and most preferably from 1:7 to 1:25. The preferred catalyst is sulfonated triphenylphosphine.

All of the materials having a lower boiling point than n-butanal (including i-butanal) are distilled out of the hydroformylation reaction mixture; as a result, the mixture is substantially free of carbon monoxide, hydrogen, propane and propene. Preferably, a distillation column having 100 to 120 theoretical plates is used, and the foregoing impurities are removed from the top of the column.

The residue is a mixture consisting almost entirely of n-butanal, but still contains 1 to 3% by weight (based on n-butanal) of n-butanol, i-butanol, aldols derived from both of the foregoing, as well as high boilers in addition to n-butanal. It is this product which is subjected to the aldol reaction without the need for any additional purification. Thus, all of the high boilers (as well as the small amount of i-butanal) remain in the reaction mixture for the aldol condensation step.

The condensation takes place in the presence of dilute, aqueous alkali hydroxide solutions. The first step produces the butyraldol, with water being split off. The reaction may take place at 80° to 170° C., particularly 90° to 160°, and most preferably at 130° to 150° C. The pressure will normally depend upon the temperature employed, but will usually be in the range of 0.1 to 0.7 MPa. The reaction time is from 0.2 to 5 minutes, preferably 0.5 to 4 minutes, and most preferably 1 to 3 minutes. The aqueous alkali hydroxide solution advantageously has a concentration of 0.5 to 5% by weight, particularly 0.8 to 4% by weight, and most preferably 1 to 2% by weight.

It has been found desirable that the n-butanal containing substances and the aqueous alkali solution be thoroughly and intensively mixed with one another. A satisfactory way to insure this is, for example, by the use of an agitator equipped vessel or a mixing pump having a downstream mixing section.

Since the 2-ethyl-hexenal is substantially insoluble in water, it is easily separated from the aqueous phase after cooling. The latter can be recycled to the condensation reaction, along with fresh aqueous alkali and n-butanal.

As one-stage hydrogenation of the raw 2-ethyl-hexenal does not produce the end product in sufficient purity as to be commercially valuable whether in the liquid or the gas phase, hydrogenation of the raw 2-ethylhexenal is conducted in two subsequent stages.

More specifically, hydrogenation, in accordance with the present invention, is carried out first in the gas phase and then in the liquid phase. The hexenal resulting from the aldol condensation is heated, passed over a suitable catalyst (preferably fixed bed) to effect the first hydrogenation step. Although it is not a necessary part of the process, solvents such as hydrocarbons, alcohols, or the like may be used.

Copper-containing catalysts have been found to be operable, particularly those which contain 40 to 75% copper by weight. Preferably, the catalyst should have 50% to 70% by weight, most preferably 55% to 65% by weight, based on the total catalyst mass. Temperatures should be approximately 110° to 180° C., more desirably 130° to 170° C., and most preferably 140° to 165° C. As previously indicated, the pressure will vary depending upon the temperature.

As carriers for the catalyst, such materials as pumice, aluminum oxide, kieselguhr, alum earth, and $SiO_2$ have been found satisfactory. Such materials as alkaline earths, aluminum, zinc and/or chromium have been found suitable as activators. The space velocity (the ratio of liquid product volume to bulk catalyst volume per hour) is desirably 0.2 to 0.6, more preferably 0.3 to 0.5, and most preferably 0.35 to 0.45 per hour. Under the foregoing conditions, it has been found that the conversion and selectivity are each more than 99%.

The second hydrogenation is carried out in the liquid phase in the presence of a nickel-containing catalyst. The temperatures are approximately 100° to 180° C., particularly 120° to 140° C., and most preferably 125° to 135° C. The pressure may be 1 to 10 MPa, more particularly 1.5 to 5 MPa, and most preferably 2.0 to 3.0 MPa. The catalyst advantageously contains 40% to 70% by weight, particularly 45% to 65% by weight, and most preferably 55% to 62% by weight of nickel, based upon the total catalyst. As in the previously-described catalyst, suitable carriers are pumice, aluminum oxide, kieselguhr, alum earth, and $SiO_2$. The same activators, e.g. alkaline earth, aluminum, zinc, and/or chromium may be used. The space velocity is 0.5 to 1.5, preferably 0.8 to 1.3, and most preferably 0.8 to 1.1 per hour. It has been found that both conversion and selectivity are virtually quantitative.

After the hydrogenated product has been distilled, the pure 2-ethyl-hexanol has excellent color and color fastness, as well as high purity. It is totally suitable and acceptable for the production of plasticizers such as dioctylphthalate.

To illustrate the present invention more particularly, reference is made to the following example:

HYDROFORMYLATION OF PROPENE

Propene and an aqueous solution containing rhodium and sulfonated triphenylphosphine are added together in the ratio of 1 part propene by volume to 8.75 parts by volume of the aqueous solution per hour. The catalyst contains approximately 400 mg Rh/l, 300 g triphenylphosphine trisulfonate. After hydroformylation, the organic phase, which contains the desired product, is separated from the aqueous catalyst phase and removed from the system. The aqueous phase is recycled to the hydroformylation reaction.

Temperature: 115° to 125° C.
Pressure: 50 bar, $CO/H_2 = 1:1$
Residence period: approximately 30 minutes.
The raw product contains:
i-$C_4$-aldehyde: 5.0% by weight
n-$C_4$-aldehyde: 94.0% by weight
Higher boilers: 1.0% by weight.

DISTILLATION OF RAW HYDROFORMYLATION MIXTURE

Separation is carried out in a column having 100 theoretical plates under the following conditions:
Pressure: 50 to 80 kPa
Temperature:
 head: 60° to 70° C.
 bottom: 90° to 100° C.
The distillation products have the following compositions:
(A) Overhead:
 i-$C_4$-aldehyde: 99.9% by weight n-C₄-aldehyde: 0.1% by weight
(B) Bottoms (residue)
  i-butanal: 0.2% by weight
  n-butanal: 98.8% by weight

| n-butanol<br>i-butanol<br>aldols<br>higher boilers | } 1.0% by weight |
|---|---|

Aldol Condensation of (B)
1,000 parts (B)
  10 parts aqueous NaOH (20% by weight).

The residue mixture and sodium hydroxide are fed into a mixing pump, mixed there, and then conveyed to a downstream mixing section. The temperature maintained is 130° to 150° C. for a residence period of approximately 3 minutes. The product is cooled after it leaves the mixing section, and phase separation is carried out at about 60° C. The aqueous phase contains about 1% to 2% by weight NaOH, and is returned to the aldol reaction. The organic phase, which contains more than 93% by weight of 2-ethyl-hexenal is then hydrogenated.

HYDROGENATION OF 2-ETHYL-HEXENAL

The hydrogenation of the unsaturated aldehyde is carried out in two successive stages. In the first stage, the aldehyde is converted to a gas by heating, and is then hydrogenated in the presence of a fixed bed copper-containing hydrogenation catalyst. The catalyst used was Cu 60/35, a product of Hoechst AG, having $SiO_2$ as a carrier. The catalyst contains approximately 60% by weight copper and about 10% by weight $SiO_2$. The reaction was carried out under the following conditions:

Temperature: 140° to 160° C.
Space velocity: 0.4 (liquid product volume/catalyst volume per hour)
Pressure: depends on temperature.

The second hydrogenation step is carried out in the liquid phase. The catalyst used is Ni 55/5, which is a product of Hoechst AG and has about 55% to 60% by weight Ni, based on the total catalyst. About 30% by weight $SiO_2$ is the carrier. This hydrogenation is carried out under the following conditions:

Temperature: 120° to 140° C.
Pressure: 2 to 2.5 MPa
Space velocity: 0.8 to 1.1.

Thereafter, the usual final distillations are carried out. Three columns are used; in the first column, the compounds having lower boiling points than 2-ethyl-hexanol are separated and, in the second column, pure 2-ethyl-hexanol is recovered in the overhead. The third column serves to separate the reusable after-run.

The yield was 97.74% of theoretical, based on the n-butanal used. However, it was noted that, if the n-butanal is separated from the high boilers before being subjected to the adol condensation, and the present procedure is otherwise followed, the yield is only 96.77% of theoretical.

Although only a limited number of embodiments of the present invention have been expressly described, it is, nonetheless, to be broadly construed, and not to be limited except by the character of the claims appended hereto.

What we claim is:

1. A process for the production of 2-ethyl-hexanol comprising reacting propene with carbon monoxide and hydrogen, in the presence of an aqueous catalyst containing rhodium and at least one sulfonated triaryl phosphine, to form an aqueous phase and an organic phase,
   said organic phase comprising a mixture of materials having boiling points lower than that of n-butanal and substances having boiling points equal to or higher than that of n-butanal, said materials including i-butanal,
   separating said material from said substances, subjecting said substances to aldol condensation, in the presence of aqueous alkali, to form 2-ethyl hexenal,
   first hydrogenating said 2-ethyl-hexenal in a gas phase in the presence of a first hydrogenation catalyst and thereafter hydrogenating said 2-ethyl-hexenal in a liquid phase to form 2-ethyl-hexanol in the presence of a second hydrogenation catalyst.

2. The process of claim 1 wherein said separating is by distillation and said substances are in the residue.

3. The process of claim 1 wherein said first catalyst is a fixed bed catalyst.

4. The process of claim 1 wherein said reaction of propene with carbon monoxide and hydrogen takes place at temperatures of 50° to 140° C., pressure of 0.1 MPa to 30 MPa, a molar ratio of said rhodium to said sulfonated triarylphosphine of from 1:3 to 1:300, and a volume ratio of said organic phase to said aqueous phase of from 1:1 to 1:100.

5. The process of claim 2 further comprising carrying out said distillation in a column having 100 to 120 theoretical plates and withdrawing said substance from the bottom of said column.

6. The process of claim 1 wherein said aqueous alkali is taken from the class consisting of 0.5% to 5% by weight solutions of LiOH, NaOH, and KOH, said aldol condensation is carried out at a temperature of 80° to 170° C. with a residence period of 0.2 to 5.0 minutes for said substances.

7. The process of claim 1 wherein said first catalyst contains copper and said first hydrogenation is carried out at 110° C. to 180° C. under pressures of 0.05 to 0.5 MPa.

8. The process of claim 7 wherein said first catalyst contains 40% to 75% by weight copper, based on the total weight of said first catalyst.

9. The process of claim 1 wherein said second hydrogenation is carried out at 100° C. to 180° C. under pressure of 1 to 10 MPa, said second catalyst containing nickel.

10. The process of claim 9 wherein said second catalyst contains 40 to 70% by weight nickel, based on the total weight of said second catalyst.

* * * * *